United States Patent
McNaughton

(10) Patent No.: US 6,823,862 B2
(45) Date of Patent: Nov. 30, 2004

(54) FLOW INDICATOR

(75) Inventor: John Peter McNaughton, Essex (GB)

(73) Assignee: Fyne Dynamics Ltd, Harlow (GB)

( * ) Notice: Subject to any disclaimer, the term of this patent is extended or adjusted under 35 U.S.C. 154(b) by 0 days.

(21) Appl. No.: 10/370,847

(22) Filed: Feb. 21, 2003

(65) Prior Publication Data
US 2003/0159694 A1 Aug. 28, 2003

(30) Foreign Application Priority Data
Feb. 25, 2002 (GB) .............................. 0204328

(51) Int. Cl.[7] .............................. A61M 11/00
(52) U.S. Cl. ..................... 128/200.22; 128/203.15; 128/203.24; 128/204.23; 128/205.23
(58) Field of Search .............. 128/200.22, 203.15, 128/203.24, 204.23, 205.23; 600/532, 535, 6, 8, 9; 482/13

(56) References Cited

U.S. PATENT DOCUMENTS

| | | | | |
|---|---|---|---|---|
| 5,042,467 A | * | 8/1991 | Foley ................... | 128/200.23 |
| 5,069,204 A | * | 12/1991 | Smith et al. ........... | 128/200.23 |
| 5,655,523 A | * | 8/1997 | Hodson et al. ........ | 128/203.15 |
| 5,758,638 A | * | 6/1998 | Kreamer ................ | 128/200.23 |
| 5,829,431 A | * | 11/1998 | Hannah et al. ........ | 128/201.19 |
| 5,865,172 A | * | 2/1999 | Butler et al. ........... | 128/203.12 |
| 5,937,852 A | * | 8/1999 | Butler et al. ........... | 128/203.12 |
| 6,012,454 A | * | 1/2000 | Hodson et al. ........ | 128/203.15 |
| 6,148,815 A | * | 11/2000 | Wolf ..................... | 128/205.23 |
| 6,578,571 B1 | * | 6/2003 | Watt ..................... | 128/200.14 |

* cited by examiner

Primary Examiner—Glenn K. Dawson
Assistant Examiner—Michael Mendoza
(74) Attorney, Agent, or Firm—Farjami & Farjami LLP

(57) ABSTRACT

A flow indicator (F) for an inhaler (I) comprises a housing (1) defining a mouthpiece (M2), an inlet (2) for connection to the product-dispensing chamber of the inhaler, a chamber (3) positioned between the inlet and the mouthpiece of the indicator, and an indicator member (4) movably mounted in the chamber in such a manner that inhalation at the mouthpiece of the indicator causes the indicator member to move within the chamber. The indicator member (4) is so mounted as to co-operate with a switch member (6, 9) associated with the housing (1) to provide an indication when inhalation is at an optimum rate for a given inhaler attached to the inlet (2).

22 Claims, 1 Drawing Sheet

FLOW INDICATOR

This application claims priority under 35 USC §119 from United Kingdom Application No. 0204328.9 filed in the United Kingdom Office on Feb. 25, 2002.

BACKGROUND OF THE INVENTION

Respiratory medication is widely administered to patients, especially asthmatics, using devices known as inhalers. An inhaler can take several forms, including an aerosol-powered, metered dose inhaler and a dry powder inhaler. Usually, a dry powder inhaler is powered using the patient's inhalation effort, the inhaler being both triggered and powered by the inhalation. An inhaler is usually used by a patient without supervision, this use usually being on a regular basis after an initial training period.

It is important that an inhaler is used properly, as the efficiency and efficacy of an inhaler is dependent on the patient's technique. Devices are known for aiding the training of a patient in the use of an inhaler. When training, the rate of inhalation of the patient is important, as too fast or too soft an effort will result in the medication not reaching the optimum distribution in the airways of the patient's respiratory system. Typically, a known training device uses a placebo in place of respiratory medication, and the training device is used, under supervision, to get the patient used to inhaling as close to the optimum rate for a given inhaler. Once the patient has a good compliance of the effort required, the training device is replaced by the appropriate inhaler.

The aim of the invention is to provide a device that can indicate to a patient when his inhalation flow rate has reached the optimum while that patient is using an inhaler.

SUMMARY OF THE INVENTION

The present invention provides a flow indicator for an inhaler, the flow indicator comprising a housing defining a mouthpiece, an inlet for connection to the product-dispensing chamber of an inhaler, a chamber positioned between the inlet and the mouthpiece of the indicator, and an indicator member movably mounted in the chamber in such a manner that inhalation at the mouthpiece of the indicator causes the indicator member to move within the chamber, the indicator member being so mounted as to co-operate with a switch member associated with the housing to provide an indication when inhalation is at an optimum rate for a given inhaler attached to the inlet.

In a preferred embodiment, a vane pivotally mounted within the chamber constitutes the indicator member.

Advantageously, the vane carries a magnet, and the switch member is a magnetic reed switch, the magnet and the reed switch constituting a magnetic switch.

Alternatively, the vane carries a magnet, and the switch member is constituted by a plurality of magnetic reed switches attached to the housing, a first reed switch being mounted so as to be aligned with the magnet when inhalation is at said optimum rate, the other reed switches being positioned on opposite sides of said first reed switch to indicate to the user when the inhalation rate is lower or higher than said optimum rate, the magnet and any one of the reed switches constituting a magnetic switch.

Preferably, the vane carries a counterweight which is positioned on the opposite side of the pivot to the magnet.

A spring may be provided to bias the vane away from the position indicating an optimum inhalation rate and towards the inlet. Preferably, the spring has a predetermined spring rating adapted to the optimum inhalation rate for a given user. Advantageously, the spring is chosen from a plurality of springs, each of which has a different spring rating adapted to the optimum inhalation rate of a different user.

Preferably, the flow indicator is provided with an adaptor for connecting its inlet to the mouthpiece of an inhaler.

The invention also provides an inhaler incorporating a flow indicator as defined above, wherein the inhaler is aligned with a product-dispensing chamber forming part of the inhaler.

DESCRIPTION OF THE DRAWINGS

The invention will now be described in greater detail, by way of example, with reference to the drawings, in which.

DETAILED DESCRIPTION OF THE INVENTION

Figure 1:
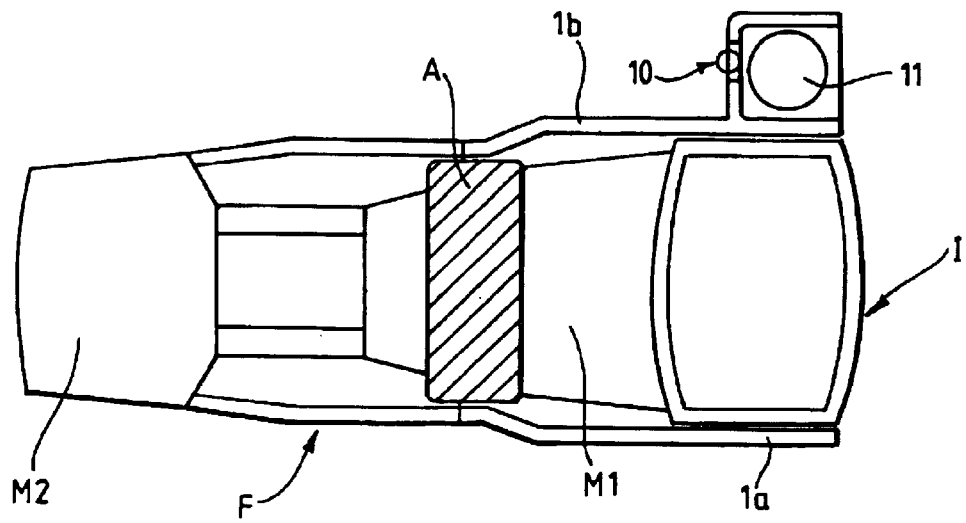
FIG. 1 is a plan view of a flow indicator constructed in accordance with the invention, the indicator being shown attached to an inhaler.

Referring to the drawings, a flow indicator F is fixed to an inhaler I by means of an adaptor A. The inhaler I is of any known type such as an aerosol-powered, metered dose inhaler or a dry powder inhaler. The inhaler I operates in a conventional manner, so this operation will not be described. The inhaler I includes a mouthpiece M1, and the adaptor A is shaped to complement the configuration of the mouthpiece. In order to facilitate connection of the flow indicator F to the inhaler I, the adaptor A is made of a soft plastics material such as polyvinyl chloride or polypropylene.

The flow indicator F has a main housing 1 made of a plastics material such as acrylonitrile-butadiene-styrene (ABS). The housing 1 defines a mouthpiece M2, through which a patient can inhale, and an inlet 2 which is contiguous with the mouthpiece M1 of the inhaler I when the flow indicator F is fixed to the inhaler by means of the adaptor A.

Figure 2:
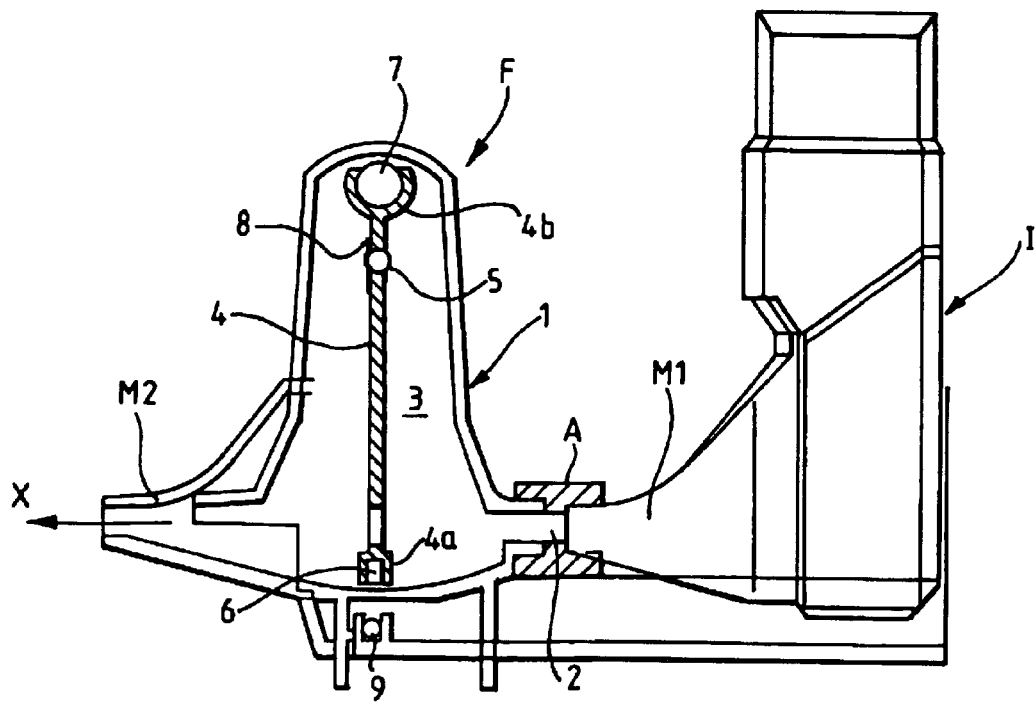
FIG. 2 is a part-sectional side elevation of the arrangement shown in FIG. 1.

The housing 1 defines a chamber 3 which houses a vane 4 made of a plastics material such as ABS. The vane 4 is pivotally mounted, at a pivot 5, to the housing 1, and is provided with a magnet 6 made of a ferrite material, the magnet being fixed within a bifurcated end portion 4a of the vane 4. The other end of portion 4b of the vane 4 is also bifurcated and houses a counterweight 7 made of brass. A coil spring 8, made of spring steel or phosphor bronze, is associated with the pivot 5, and acts to bias the vane 4 in an anticlockwise direction away from the position shown in FIG. 2. The housing 1 is provided with a two-armed extension 1a, 1b, these extension arms extending, in use, so as to engage the sides of the inhaler I. The arm 1a carries a magnetic reed switch 9 which is positioned in alignment with the central longitudinal axis of the chamber 3. The arm 1b carries an LED 10 and a battery 11.

In use, the indicator F is fixed to the inhaler I using the adaptor A. The patient then inhales via the mouthpiece M2, as indicated by the arrow X. The spring 8 is rated so that, when the patient inhales at the optimum rate, the vane 4 is substantially in alignment with the central longitudinal axis of the chamber 3, in which position the magnetic reed switch 9 is triggered by the proximity of the magnet 6, the magnetic switch completing an electrical circuit between the battery 11 and the LED 10, thereby illuminating the LED. Thus, with the indicator F attached to the inhaler I, the patient can determine the optimum inhalation rate whilst using the inhaler, it being a relatively easy learning process to increase the inhalation rate until the optimum rate is reached as indicated by the turning-on of the LED 10.

The vane 4 is counterbalanced because the indicator F/inhaler I arrangement may not always be used with the chamber 3 in a generally vertical position, the counterbalancing negating the effects of gravity when the arrangement is used in such a non-vertical configuration.

It will be apparent that the indicator F described above could be modified in a number of ways. For example, the indicator F could be provided with a plurality of magnetic reed switches, the additional switches being positioned, for example, on either side of the magnetic switch that indicates the optimum inhalation rate. The additional switches can then be used to indicate to the patient whether to inhalation rate is too low or too high, and generally by how much the inhalation rate is too high or too low. In such an arrangement, a plurality of LEDs may be used to provide the necessary indication. It would also be possible to replace the LED by any other suitable form of indicating device, for example a buzzer.

It will also be apparent that the indicator F could be modified to indicate the optimum inhalation rate of any type of inhaler. Thus, by using springs of different ratings, the indicator F could easily be modified to suit inhalers requiring different optimum inhalation rates. It would also be possible to use adaptors of different configurations to complement the mouthpieces of different inhalers.

In another modification, the indicator F would form an integral part of the inhaler I. In that case, the adaptor A and the mouthpiece M1 would not be required, and the inlet 2 would be aligned with the product-dispensing chamber of the inhaler I.

I claim:

1. A flow indicator for an inhaler, the flow indicator comprising:
   a housing defining a mouthpiece,
   an inlet for connection to a product-dispensing chamber of the inhaler,
   a chamber positioned between the inlet and the mouthpiece of the indicator, and
   an indicator member movably mounted in the chamber in such a manner that inhalation at the mouthpiece of the indicator causes the indicator member to move within the chamber, the indicator member being so mounted as to co-operate with a switch member associated with the housing to provide an indication when inhalation is at an optimum rate for a given inhaler attached to the inlet,
   wherein a vane pivotally mounted within the chamber constitutes the indicator member, and wherein the vane carries a counterweight which is positioned on the opposite side of a pivot to a magnet.

2. A flow indicator as claimed in claim 1, wherein the vane carries the magnet, and the switch member is a magnetic reed switch, the magnet and the reed switch constituting a magnetic switch.

3. A flow indicator as claimed in claim 2, further comprising an electrical circuit including the magnetic switch and a transducer.

4. A flow indicator as claimed in claim 3, wherein the transducer is an LED.

5. A flow indicator as claimed in claim 3, wherein the electrical circuit includes a battery.

6. A flow indicator as claimed in claim 1, wherein the vane carries the magnet, and the switch member is constituted by a plurality of magnetic reed switches attached to the housing, a first reed switch being mounted so as to be aligned with the magnet when inhalation is at said optimum rate, the other reed switches being positioned on opposite sides of said first reed switch to indicate to a user when an inhalation rate is lower or higher than said optimum rate, the magnet and any one of the reed switches constituting a magnetic switch.

7. A flow indicator as claimed in claim 6, further comprising an electrical circuit including the magnetic switch and a transducer.

8. A flow indicator as claimed in claim 7, wherein the transducer is an LED.

9. A flow indicator as claimed in claim 7, wherein the electrical circuit includes a battery.

10. A flow indicator as claimed in claim 1, further comprising a spring for biasing the vane away from the position indicating an optimum inhalation rate and towards the inlet.

11. A flow indicator as claimed in claim 10, wherein the spring has a predetermined spring rating adapted to the optimum inhalation rate for a given user.

12. A flow indicator as claimed in claim 11, wherein the spring is chosen from a plurality of springs, each of which has a different spring rating adapted to the optimum inhalation rate of a different user.

13. A flow indicator as claimed in claim 1, further comprising an adaptor for connecting the inlet to a mouthpiece of the inhaler.

14. A flow indicator for an inhaler, the flow indicator comprising:
    a housing defining a mouthpiece,
    an inlet for connection to a product-dispensing chamber of the inhaler,
    a chamber positioned between the inlet and the mouthpiece of the indicator, and
    an indicator member movably mounted in the chamber in such a manner that inhalation at the mouthpiece of the indicator causes the indicator member to move within the chamber, the indicator member being so mounted as to co-operate with a switch member associated with the housing to provide an indication when inhalation is at an optimum rate for a given inhaler attached to the inlet,
    wherein a vane pivotally mounted within the chamber constitutes the indicator member, and wherein the vane carries a magnet, and the switch member is constituted by a plurality of magnetic reed switches attached to the housing, a first reed switch being mounted so as to be aligned with the magnet when inhalation is at said optimum rate, the other reed switches being positioned on opposite sides of said first reed switch to indicate to a user when an inhalation rate is lower.

15. A flow indicator as claimed in claim 14, further comprising an electrical circuit including the magnetic switch and a transducer.

16. A flow indicator as claimed in claim 15, wherein the transducer as an LED.

17. A flow indicator as claimed in claim 15, wherein the electrical circuit includes a battery.

18. A flow indicator as claimed in claim 14, wherein the vane carries a counterweight which is positioned on the opposite side of a pivot to the magnet.

19. A flow indicator as claimed in claim 14, further comprising a spring for biasing the vane away from the position indicating an optimum inhalation rate and towards the inlet.

20. A flow indicator as claimed in claim 19, wherein the spring has a predetermined spring rating adapted to the optimum inhalation rate for a given user.

21. A flow indicator as claimed in claim 20, wherein the spring is chosen from a plurality of springs, each of which has a different spring rating adapted to the optimum inhalation rate of a different user.

22. A flow indicator as claimed in claim 14, further comprising an adaptor for connecting the inlet to a mouthpiece of the inhaler.

* * * * *